United States Patent
Stansell et al.

(10) Patent No.: US 6,359,689 B1
(45) Date of Patent: Mar. 19, 2002

(54) PROGRAMMABLE AUTOMATED TURBIDIMETER/COLORIMETER

(75) Inventors: Marion J. Stansell, San Antonio; Gene C. Deck, Natalia, both of TX (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 09/417,403

(22) Filed: Oct. 13, 1999

Related U.S. Application Data

(60) Provisional application No. 60/106,906, filed on Oct. 26, 1998.

(51) Int. Cl.[7] .............................................. C01N 21/59
(52) U.S. Cl. ....................................... 356/440; 356/246
(58) Field of Search ................................. 356/244, 246, 356/440

(56) References Cited

U.S. PATENT DOCUMENTS 3,551,062 A * 12/1970 Brown ....................... 356/244
3,609,047 A * 9/1971 Marlow ...................... 356/434
4,305,723 A * 12/1981 Kolber et al. ............... 356/246

* cited by examiner

Primary Examiner—Richard A. Rosenberger
(74) Attorney, Agent, or Firm—Bobby D. Scearce; Thomas L. Kundert

(57) ABSTRACT

A programmable automated turbidimeter/colorimeter system for accurately measuring growth among multiple bacterial specimens is described which in a preferred embodiment includes a motor driven rotatable carousel assembly disposed within an aluminum housing, the carousel assembly including a plurality of evenly spaced peripheral holes for receiving a corresponding plurality of disposable culture test tubes, a light source and a light detector disposed in spaced confronting relationship to each other whereby the culture tubes pass therebetween, and a signal amplifier and a recorder for recording optical densities of each specimen as the carousel is continuously rotated. A concentric magnetic shield may be disposed on one side of the carousel for shielding experimental specimens from control specimens in measurements of magnetic effects on the cultures.

4 Claims, 2 Drawing Sheets ically to a fully programmable automated turbidimeter/
PROGRAMMABLE AUTOMATED TURBIDIMETER/COLORIMETER This application claims priority of the filing date of Provisional Application Ser. No. 60/106,906 filed Oct. 26, 1998, the entire contents of which application are incorporated by reference herein.

RIGHTS OF THE GOVERNMENT

The invention described herein may be manufactured and used by or for the Government of the United States for all governmental purposes without the payment of any royalty.

BACKGROUND OF THE INVENTION

The present invention relates generally to systems and methods for culture growth and testing, and more particularly to a fully programmable automated turbidimeter/colorimeter system for accurately measuring and comparing turbidity or growth and optical density, gradually changing or stable, among multiple bacterial specimens under carefully controlled conditions.

In the course of experiments for determining the behavior of bacterial cultures treated with antibiotics and exposed to varying combinations of magnetic fields, experimental specimens were exposed to magnetic fields and identically handled control specimens were not so exposed. In those experiments it was observed that, following treatment with antibiotic, neither experimental nor control cultures showed any measurable growth for about 12 hours, after which the cultures began to show growth but at different rates. Following the progress of the culture growth and making critical measurements at prescribed time intervals therefore required the attention of laboratory personnel substantially constantly for protracted periods of time of up to eighteen hours or more. No reliable conventional system existed for making the desired measurements automatically in a substantially continuous manner.

The invention solved or substantially reduced in critical importance problems in the prior art as just suggested by providing a fully programmable automated turbidimeter/colorimeter system.

It is a principal object of the invention to provide an improved turbidimeter for measuring bacterial growth.

It is a further object of the invention to provide a lightweight and compact turbidimeter.

It is yet another object of the invention to provide a fully programmable and automated turbidimeter.

It is another object of the invention to provide a programmable automated turbidimeter for measuring the magnetic effects on bacterial culture growth.

It is yet another object of the invention to provide a programmable automated turbidimeter for measuring antibiotic effects on bacterial culture growth.

These and other objects of the invention will become apparent as a detailed description of representative embodiments proceeds.

SUMMARY OF THE INVENTION

In accordance with the foregoing principles and objects of the invention, a programmable automated turbidimeter/colorimeter system for accurately measuring growth among multiple bacterial specimens is described which in a preferred representative embodiment includes a motor driven rotatable carousel assembly disposed within an aluminum housing, the carousel assembly including a plurality of evenly spaced peripheral holes for receiving a corresponding plurality of disposable culture test tubes, a light source and a light detector disposed in spaced confronting relationship to each other whereby the culture tubes pass therebetween, and a signal amplifier and a recorder for recording optical densities of each specimen as the carousel is continuously rotated. A concentric magnetic shield may be disposed on one side of the carousel for shielding experimental specimens from control specimens in measurements of magnetic effects on the cultures.

DESCRIPTION OF THE DRAWINGS

The invention will be more clearly understood from the following detailed description of representative embodiments thereof read in conjunction with the accompanying drawings wherein.

DETAILED DESCRIPTION

Background information related to the invention and reports of experimental work utilizing a turbidimeter built in demonstration of the invention are presented in Stansell et al, "Increased Antibiotic Resistance of *E. coli* Exposed to Static Magnetic Fields," (submitted for publication in the *Journal of Bioelectromagnetics*), the entire contents and teachings of which are incorporated by reference herein.

Figures 1, 1A:
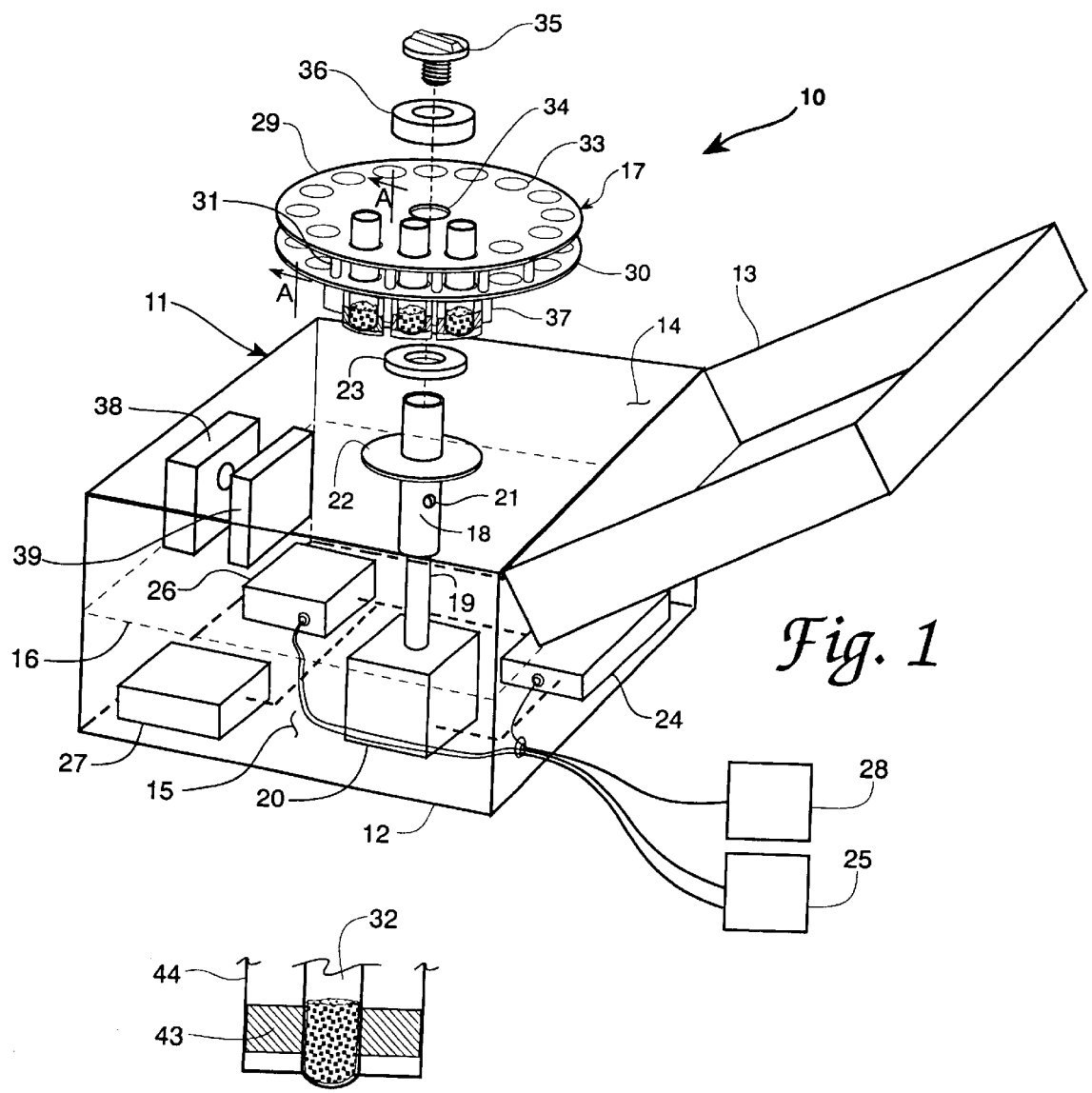
FIG. 1 is a partially exploded view of the essential components of a representative embodiment of the turbidimeter system of the invention built and operated in demonstration thereof.
FIG. 1a is a view of the demonstration system of FIG. 1 taken along lines A—A thereof.

Referring now to the drawings, FIG. 1 shows a partially exploded view of the essential components of a representative embodiment of a turbidimeter system 10 built and operated in demonstration of the invention. Demonstration system 10 included a housing 11 having a body portion 12 and optional hinged lid 13 for closure of housing 11, housing 11 preferably comprised of aluminum, wood, opaque plastic or other opaque non-ferrous material (the selected material should be opaque in order to exclude stray light) (in the demonstration system, portion 12 was 27×27 cm×15.5 cm high and lid 13 was 27×27 cm×7.5 cm high, and housing 11 was fabricated of aluminum, however, size and materials of construction are not considered limiting of the invention). Body portion 12 was divided into substantially equal volume upper and lower compartments 14,15 separated by horizontal wall member 16.

A rotatable carousel assembly 17 was disposed within upper compartment 14 and mounted for rotation on an aluminum sleeve 18 secured to drive shaft 19 extending through wall member 16 from motor 20 in lower compartment 15 substantially as shown in FIG. 1. Sleeve 18 may be secured to drive shaft 19 by suitable means such as set screws 21. Flange 22 and spacer 23 supported carousel assembly 17 on sleeve 18. Motor 20 may comprise any commercially available variable speed carousel drive motor suitable for the intended function, a Hurst Model PA 115 volt AC motor being selected for use in the demonstration system. Power supply 24 was disposed within lower compartment 15 and operatively connectable to a suitable external source 28 of electrical power. Power supply 24 provides regulated voltages for differential amplifier 26, and timer/ controller module 27 (Macromatic Time Delay Relay, SS65122, #9OF1397, Repeat Program Cycle Timer, in the demonstration system). The output from differential amplifier 26 connects to recorder amplifier and/or computer 25. Suitable controls (not shown) were panel mounted in an outer wall of housing 11 and operatively connected to components 20,24,26,27 within lower compartment 15 for regulating amplifier gain, zero/100% transmittance positioning, on-cycle-off-cycle duration control, carousel rotation direction, power on/off, and recorder amplifier and/or computer inputs.

In the FIG. 1 demonstration system, carousel assembly 17 comprised a pair of plastic disk members 29,30 (each 23.8 cm dia×0.4 cm thick) held in spaced relationship (about 2.7 cm in the demonstration system) by a plurality of spacers 31. A plurality (16 in the demonstration system) of evenly spaced holes 33 were defined in the periphery of disk members 29, 30 substantially as shown in FIG. 1, for receiving a corresponding plurality of disposable culture test tubes 32 as described more fully below in relationship to FIG 1a. A central hole 34 in carousel assembly 17 was sized to receive aluminum sleeve 18 and carousel assembly was secured to sleeve 18 by set screw 35 and washer 36 for rotation with sleeve 18 and drive shaft 19 of motor 20. Carousel assembly 17 was disposed in selected spaced relationship to wall member 16 by placement of a selected number of spacers 23. In the FIG. 1 system, holes 33 were sized to receive 17 mm diameter sterile plastic cappable culture tubes, although specific tube size is not considered limiting of the invention. Smaller diameter tubes could be used by inserting sleeves of appropriate inner/outer diameters within holes 33 for snugly receiving the smaller diameter tubes.

Concentric with the drive shaft hole 34 was placed a mu-metal shield (magnetic shielding) 37 to effectively isolate tubes containing control specimens on one side of carousel plate 17 from tubes with magnets containing experimental specimens on the other side. Shield 37 is used in applications involving the effects of magnetic fields on bacterial resistance to drugs as discussed below. FIG. 1a is a view along lines A—A of FIG. 1 of an experimental tube 32 and cylindrical magnet 43 assembly in place in carousel assembly 17. Cylindrical magnets 43 may be cemented to a formed sheet copper frame 44 bent in the shape shown, and the assembly may be compression fitted to culture tube 32.

Figure 2:
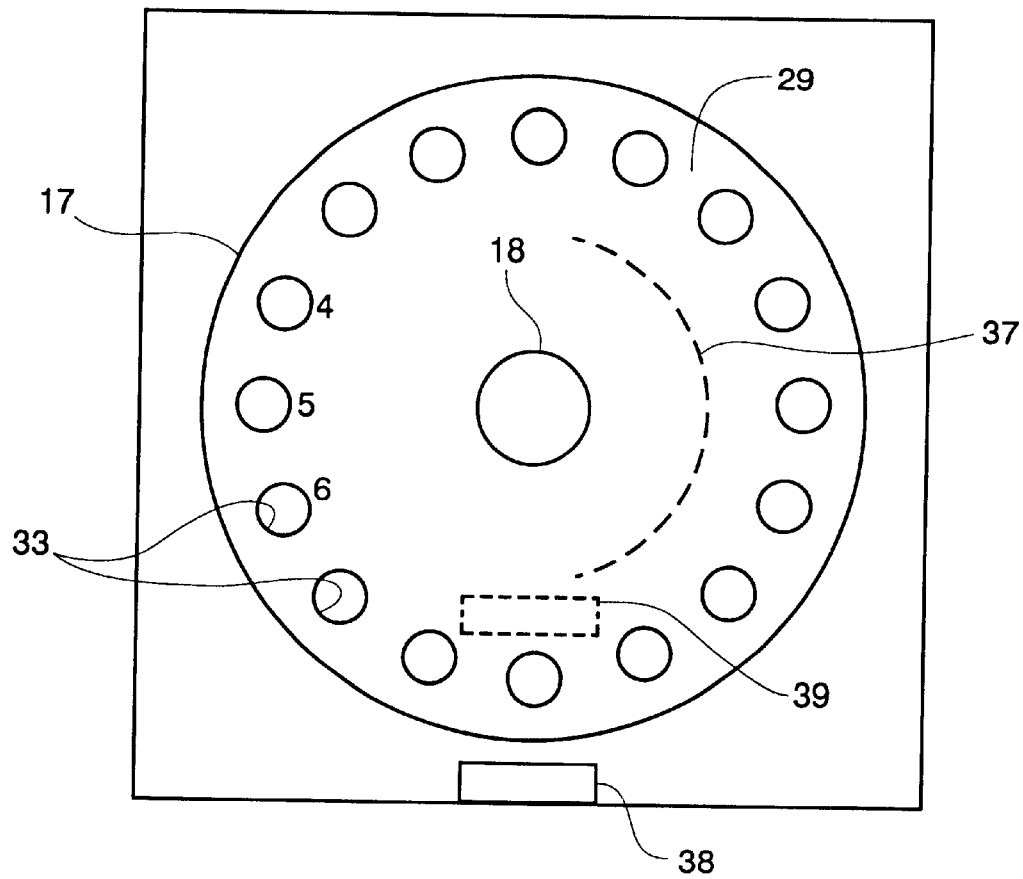
FIG. 2 is a top view of the carousel assembly of the FIG. 1 demonstration system.

Upper compartment 14 (FIG. 1) includes a light source 38 disposed substantially as shown in FIG. 1 near one side wall of housing 11, and light detector 39 was disposed in confronting relationship to light source 38 and movably spaced (2.2 cm in the demonstration system) from source 38 sufficiently to allow tubes 32 to pass therebetween as carousel 17 is rotated. FIG. 2 shows a top view of carousel 17 and housing 11 of the FIG. 1 system illustrating the positions of source 38, detector 39, shield 37 and upper disk member 29. In the demonstration system, light source 38 comprised one or more high intensity light emitting diodes (LED) and detector was a photodiode (PD) (VTB 6061, max 2000 pA dark current in the demonstration system), although other sources and detectors may be selected by a skilled artisan practicing the invention, such as an incandescent lamp, ultraviolet deuterium lamp, or infrared glower sources and visible range, ultraviolet specific or infrared specific detectors, the same not considered limiting of the invention. Amplifier 26 processed the output from detector 39. Operation of system 10 may be preprogrammed and fully computer controlled, including the timing and stop/go control of carousel 17 rotation, system on/off periods, selection and control of light source 38, detector 39 operation and the acquisition and analysis of culture growth data derived from the operation of system 10.

In a typical application of the turbidimeter system of the invention such as described in Stansell et al, supra, bacteria (clinical isolate of *E. coli*) from a pure culture are inoculated into trypticase soy broth (TSB) at a concentration of $1.5 \times 10^8$ cfu/ml and grown at 37° C. until density reaches about $8 \times 10^8$ cfu/ml. The culture is then diluted with fresh TSB to $1.5 \times 10^8$ cfu/ml and allowed to grow at 37° C. until the density again reaches $8 \times 10^8$ cfu/ml. Then the culture is diluted once again with fresh TSB to give $1.5 \times 10^8$ cfu/ml and then further diluted 1000:1 to a concentration of $1.5 \times 10^5$ cfu/ml at 37°. Two ml aliquots of the diluted culture are transferred to prewarmed (37° C.) tubes mounted in carousel assembly 17. Magnet and/or sham assemblies are attached to tubes 32 as appropriate. Carousel assembly 17, with filled tubes, is immediately returned to the incubator and the aliquoted cultures allowed to grow for 90 minutes at 37° C. After the initial incubation, caps of tubes 32 are temporarily removed and standardized quantities of antibiotic solution are added with mixing. The caps are replaced and the timer controls set for desired on-time/off-time durations.

Carousel assembly 17 rotates at any preselected speed (one rpm in the tests performed in the demonstration system) and the sensitivity is set to give a full scale reading (with pure TSB in the path) on the 0–5 volt scale of the strip chart recorder. The use of high output voltage from the differential amplifier provides an excellent signal to noise ratio. In addition to a selected number of experimental tubes 32 and a corresponding number of control tubes 32, carousel assembly 17 may contain an opaque tube to set the baseline to zero transmittance and a tube containing pure TSB to set transmittance to 100%. As the center of a tube 32 passes through the light beam from source 38, transmittance of the tube 32 reaches a maximum. The transmittance is a measure of the amount of turbidity (bacterial growth) in the specimen contained in the tube. As growth continues over time, the transmittance gradually decreases until a plateau is reached, indicating exhaustion of the TSB and stationary phase in the bacterial growth cycle. Additional experimental tests utilizing turbidimeter 10 are presented in Stansell et al, supra.

The invention therefore provides a fully programmable automated turbidimeter. It is understood that modifications to the invention may be made as might occur to one with skill in the field of the invention, within the scope of the appended claims. All embodiments contemplated hereunder that achieve the objects of the invention have therefore not been shown in complete detail. Other embodiments may be developed without departing from the spirit of the invention or from the scope of the appended claims.

We claim:

1. A turbidimeter system for accurately measuring growth among multiple bacterial specimens, comprising:
    (a) a substantially closed housing;
    (b) a motor driven rotatable carousel assembly disposed within said housing, said carousel assembly having defined in the periphery thereof a plurality of evenly spaced holes for receiving a corresponding plurality of test tubes;
    (c) a light source and a light detector disposed within said housing below said carousel, said light source and light detector disposed in spaced confronting relationship to each other for allowing the test tubes to pass therebetween as said carousel is rotated;
    (d) a signal amplifier and a recorder for recording optical densities of specimens contained within the test tubes as said carousel is rotated; and (e) a magnetic shield disposed on one side of the carousel for magnetic shielding of test tubes on one side of said carousel from test tubes on the diametrically opposite side of said carousel.

2. The system of claim 1 wherein said light source comprises one or more light emitting diodes, and incandescent lamp, ultraviolet deuterium lamp, or infrared glower source.

3. The system of claim 1 wherein said detector comprises a photodiode.

4. The system of claim 1 wherein said housing comprises a non-ferrous opaque material selected from the group consisting of aluminum, wood, and plastic.

* * * * *